(12) United States Patent
Walker (10) Patent No.: US 9,839,529 B2
(45) Date of Patent: Dec. 12, 2017

(54) METHOD AND SYSTEM OF INSTALLING A SPINAL FUSION CAGE

(71) Applicant: Zavation, LLC, Flowood, MS (US)

(72) Inventor: John Lawrence Walker, Madison, MS (US)

(73) Assignee: Zavation Medical Products, LLC, Flowood, MO (US)

(*) Notice: Subject to any disclaimer, the term of this patent is extended or adjusted under 35 U.S.C. 154(b) by 31 days.

(21) Appl. No.: 15/156,517

(22) Filed: May 17, 2016

(65) Prior Publication Data

US 2016/0338846 A1    Nov. 24, 2016

Related U.S. Application Data

(60) Provisional application No. 62/162,973, filed on May 18, 2015.

(51) Int. Cl.
*A61F 2/44* (2006.01)
*A61F 2/46* (2006.01)

(52) U.S. Cl.
CPC ............ *A61F 2/447* (2013.01); *A61F 2/4611* (2013.01); *A61F 2002/4475* (2013.01); *A61F 2220/0016* (2013.01)

(58) Field of Classification Search
CPC ....... A61F 2/447; A61F 2/4611; A61F 2/4475
See application file for complete search history.

(56) References Cited

U.S. PATENT DOCUMENTS

| | | | |
|---|---|---|---|
| 7,708,778 B2 | 5/2010 | Gordon et al. | |
| 7,883,542 B2 | 2/2011 | Zipnick | |
| 7,951,199 B2 | 5/2011 | Miller | |
| 8,088,163 B1* | 1/2012 | Kleiner | A61F 2/4465 623/17.11 |
| 2007/0129719 A1* | 6/2007 | Kendale | A61B 1/00096 606/41 |
| 2008/0039948 A1* | 2/2008 | Biedermann | A61F 2/44 623/17.16 |
| 2008/0140085 A1* | 6/2008 | Gately | A61F 2/4465 606/99 |
| 2010/0082106 A1* | 4/2010 | Muhanna | A61F 2/442 623/17.11 |

(Continued)

*Primary Examiner* — Ellen C Hammond
*Assistant Examiner* — Stuart S Bray
(74) *Attorney, Agent, or Firm* — Tarolli, Sundheim, Covell & Tummino LLP (57) ABSTRACT

A method and system are provided for installing a spinal fusion cage. The spinal fusion cage includes an outer cage having a proximal outer cage endwall and a distal outer cage endwall. An inner cage has a proximal inner cage endwall and a distal inner cage endwall. The proximal and distal inner cage endwalls each are in slidable contact with a corresponding one of the proximal and distal outer cage endwalls. The inner and outer cages collectively define a fusion cage cavity space having a volume which varies responsive to relative sliding of the inner cage with respect to the outer cage. An actuation tool includes a shaft and an operative portion. The operative portion of the actuation tool has an asymmetrically tapered portion which includes a longitudinally aligned face extending substantially parallel to the longitudinal axis and an angled face extending at an acute angle to the longitudinal axis.

21 Claims, 8 Drawing Sheets

(56) References Cited

U.S. PATENT DOCUMENTS

| | | | |
|---|---|---|---|
| 2010/0114105 A1* | 5/2010 | Butters | A61F 2/4611 606/99 |
| 2011/0202135 A1* | 8/2011 | Baek | A61F 2/4611 623/17.16 |
| 2012/0150301 A1* | 6/2012 | Gamache | A61B 17/1631 623/17.16 |
| 2012/0226356 A1* | 9/2012 | Hirschl | A61F 2/4455 623/17.16 |
| 2013/0023994 A1* | 1/2013 | Glerum | A61F 2/447 623/17.16 |
| 2013/0211525 A1* | 8/2013 | McLuen | A61F 2/4455 623/17.16 |
| 2013/0274883 A1* | 10/2013 | McLuen | A61F 2/447 623/17.16 |
| 2014/0148904 A1* | 5/2014 | Robinson | A61F 2/447 623/17.16 |
| 2014/0277459 A1* | 9/2014 | McCarthy | A61F 2/4611 623/17.11 |
| 2014/0277496 A1 | 9/2014 | Ammerman | |
| 2015/0012097 A1* | 1/2015 | Ibarra | A61F 2/447 623/17.15 |
| 2015/0148908 A1* | 5/2015 | Marino | A61F 2/4455 623/17.16 |
| 2015/0223946 A1* | 8/2015 | Weiman | A61F 2/447 623/17.15 |
| 2015/0297358 A1 | 10/2015 | Perisic | |
| 2016/0030190 A1* | 2/2016 | Robinson | A61F 2/447 623/17.16 |
| 2016/0038305 A1* | 2/2016 | Weiman | A61F 2/4455 623/17.16 |
| 2016/0175108 A1* | 6/2016 | Howard | A61F 2/442 623/17.14 |
| 2016/0296344 A1* | 10/2016 | Greenhalgh | A61F 2/4601 |
| 2017/0014244 A1* | 1/2017 | Seifert | A61F 2/4455 |
| 2017/0056197 A1* | 3/2017 | Weiman | A61F 2/447 |
| 2017/0119541 A1* | 5/2017 | Greenhalgh | A61F 2/447 |
| 2017/0119543 A1* | 5/2017 | Dietzel | A61F 2/447 |
| 2017/0165083 A1* | 6/2017 | Greenhalgh | A61F 2/447 |

* cited by examiner

METHOD AND SYSTEM OF INSTALLING A SPINAL FUSION CAGE

RELATED APPLICATION

This application claims priority from U.S. Provisional Application No. 62/162,973, filed 18 May 2015, the subject matter of which is incorporated herein by reference in its entirety.

TECHNICAL FIELD

This disclosure relates to a method and system for installing a spinal fusion cage, and, more particularly, to a system and method for installing a laterally expandable spinal fusion cage.

BACKGROUND

Eighty five percent of the population will experience low back pain at some point. Fortunately, the majority of people recover from their back pain with a combination of benign neglect, rest, exercise, medication, physical therapy, and/or chiropractic care. A small percentage of the population will suffer chronic low back pain. The cost of treatment of patients with spinal disorders, plus the patients' lost productivity, is estimated to be 25 to 100 billion dollars annually.

Seven cervical neck, twelve thoracic, and five lumbar (low back) vertebrae form the normal human spine. Intervertebral discs reside between adjacent vertebrae with two exceptions: (1) the articulation between the first two cervical vertebrae does not contain a disc; and (2) a disc lies between the last lumbar vertebra and the sacrum (a portion of the pelvis).

Motion between vertebrae occurs through the disc and two facet joints. The disc lies in the front or anterior portion of the spine. The facet joints lie laterally on either side of the posterior portion of the spine. The osseous-disc combination of the spine coupled with ligaments, tendons and muscles are essential for spinal function. The spine allows movement (flexion, lateral bending, and rotation), supports the body, and protects the spinal cord and nerves.

The discs change with aging. As a person ages, the water content of the disc falls from approximately 85 percent at birth to about 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration.

Premature or accelerated disc degeneration is known as degenerative disc disease. A large portion of patients suffering from chronic low back pain are through to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in bulging of the annulus into the spinal cord or nerves, narrowing of the space between the vertebra where the nerves exit, tears of the annulus as abnormal loads are transmitted to the annulus and the annulus is subjected to excessive motion between vertebra, and/pr disc herniation or extrusion of the nucleus through complete annular tears. Disc herniation can also promote arthritis of the facet joints, which in turn may cause back pain.

The problems created by disc degeneration, facet arthritis, and other conditions such as spondylolysis, spondylolisthesis, scoliosis, fracture, tumor, or infection are frequently treated by spinal fusion. Such problems may include pain in the back or legs, nerve injury, risk of future nerve injury, or spinal deformity. The goal of spinal fusion is to successfully "grow" two or more vertebrae together. To achieve this, bone from the patient's body (spine or iliac crest), or from cadavers, is grafted between vertebrae. Alternatively, bone graft substitutes, such as hydroxyl apatite and bone morphogenic protein, may be used. Any autograft, allograft, cadaver graft, bone graft substitutes, or other materials which are placed between the vertebrae to encourage bony fusion will be collectively referenced herein as "graft" or "bone graft".

The bone graft is placed between the vertebrae in the disc space and/or over the posterior elements of the vertebrae (lamina and transverse processes). The surgeon scrapes the vertebrae to create bleeding. Blood flows into the bone gage. The scraped bone, blood clot (hematoma), and the bone graft simulates a fracture. As the patient heals, the "fracture" causes the vertebrae to be fused and heal together.

Spinal instrumentation, including cages, may be placed onto or into the spine to immobilize the vertebrae that are going to be fused. Immobilization leads to a higher fusion rate and speeds a patient's recovery by eliminating movement. Existing cages are typically hollow metal or carbon fiber devices placed into the disc space. Often, cages have treads, grooves, and teeth or spikes that engage the cerebral endplates. The hollow center of the cage may be filled with a bone graft. The sides of the cages adjacent to the vertebral end plates contain holes to allow bone growth from one vertebra through the cage to the adjacent vertebra. The bone graft acts as a bridge for bone growth. Cages immobilize the vertebrae and maintain the separation between the vertebrae, a function of the formed disc material. Cages are placed into the disc space after excising a portion of the disc annulus and most of the nucleus. One or two cages may be inserted at each level.

Cages may be placed into the disc space from an anterior or a posterior approach to the spine. Cages may be combined with rods, screws, hooks, plates, or other structures. Combining cages with other instrumentation yields a stiffer construct and presumably increases the chance for a successful fusion. If cages are placed from an anterior approach (through the abdomen), the patient must undergo surgery through a second incision over the back (posterior approach) if the surgeon wishes also to insert rods and screws. To avoid two incisions and increased patient morbidity, many surgeons prefer to insert cages from a posterior approach. Rods and screws can then be added through the same incision.

SUMMARY

In an aspect, a method of installing a spinal fusion cage is described. A spinal fusion cage is provided. The spinal fusion cage includes an outer cage having a proximal outer cage endwall longitudinally spaced from a distal outer cage endwall. The proximal outer cage endwall includes a tool aperture. The outer cage includes an outer cage sidewall extending longitudinally between the proximal and distal outer cage endwalls. An inner cage has a proximal inner cage endwall longitudinally spaced from a distal inner cage endwall. The inner cage includes an inner cage sidewall extending longitudinally between the proximal and distal inner cage endwalls. The proximal and distal inner cage endwalls each are in slidable contact with a corresponding one of the proximal and distal outer cage endwalls. The proximal and distal inner cage endwalls each include an endwall contact surface at a laterally opposite face of the proximal and distal inner cage endwalls from the inner cage sidewall. The inner cage selectively slides with respect to the outer cage to transition the spinal fusion cage between retracted and expanded configurations. The inner and outer cages collectively define a fusion cage cavity space. The fusion cage cavity space has a volume which varies responsive to relative sliding of the inner cage with respect to the outer cage. An actuation tool is provided. The actuation tool includes a shaft having a shaft cross-sectional area, taken perpendicular to a longitudinal axis. An operative portion of the actuation tool, located longitudinally distal to the shaft, is configured for at least partial insertion in a distal direction through the tool aperture into the fusion cage cavity space. The operative portion of the actuation tool has an asymmetrically tapered portion. A distal end of the asymmetrically tapered portion has a first cross-sectional area, taken perpendicular to the longitudinal axis, which is smaller than the shaft cross-sectional area. The asymmetrically tapered portion includes a longitudinally aligned face extending substantially parallel to the longitudinal axis and an angled face extending at an acute angle to the longitudinal axis and oriented in lateral opposition to the longitudinally aligned face. The spinal fusion cage is placed, in the retracted configuration, between two adjacent vertebrae of a patient. The actuation tool is longitudinally aligned with the tool aperture, with the longitudinally aligned face being directly adjacent an inner face of the outer cage sidewall, and the operative portion of the actuation tool being longitudinally interposed between the shaft of the tool and the spinal fusion cage. The distal end of the operative portion of the actuation tool is inserted into the fusion cage cavity space via the tool aperture. The inner face of the outer cage sidewall is contacted with the longitudinally aligned face of the actuation tool in a sliding manner. The endwall contact surface of the proximal inner cage endwall is contacted with the angled face of the actuation tool in a sliding manner. The endwall contact surface of the proximal inner cage endwall is urged laterally apart from the outer cage sidewall into an at least partially expanded configuration via wedging action of the actuation tool sliding longitudinally into and through the fusion cage cavity space. The actuation tool is imposed laterally between the proximal inner cage endwall and the outer cage sidewall. With the actuation tool being imposed laterally between the proximal inner cage endwall and the outer cage sidewall, the operative portion of the actuation tool is further inserted into the fusion cage cavity space via the tool aperture to achieve a predetermined depth of insertion of the actuation tool into the spinal fusion cage. The actuation tool is rotated, at the predetermined depth of insertion, a predetermined amount about the longitudinal axis to bring the distal end of the operative portion of the actuation tool into contact with the distal inner cage endwall. The endwall contact surface of the distal inner cage endwall is urged laterally apart from the outer cage sidewall into an at least partially expanded configuration via contact with the operative portion of the actuation tool during rotation of the actuation tool.

In one aspect, a system for installing a spinal fusion cage is provided. The spinal fusion cage includes an outer cage having a proximal outer cage endwall longitudinally spaced from a distal outer cage endwall. The proximal outer cage endwall includes a tool aperture. The outer cage includes an outer cage sidewall extending longitudinally between the proximal and distal outer cage endwalls. An inner cage has a proximal inner cage endwall longitudinally spaced from a distal inner cage endwall. The inner cage includes an inner cage sidewall extending longitudinally between the proximal and distal inner cage endwalls. The proximal and distal inner cage endwalls each are in slidable contact with a corresponding one of the proximal and distal outer cage endwalls. The proximal and distal inner cage endwalls each include an endwall contact surface at a laterally opposite face of the proximal and distal inner cage endwalls from the inner cage sidewall. The inner cage selectively slides with respect to the outer cage to transition the spinal fusion cage between retracted and expanded configurations. The inner and outer cages collectively define a fusion cage cavity space. The fusion cage cavity space has a volume which varies responsive to relative sliding of the inner cage with respect to the outer cage. An actuation tool includes a shaft having a shaft cross-sectional area, taken perpendicular to a longitudinal axis. An operative portion of the actuation tool is located longitudinally distal to the shaft and is configured for at least partial insertion in a distal direction through the tool aperture into the fusion cage cavity space. The operative portion of the actuation tool has an asymmetrically tapered portion. A distal end of the operative portion has a first cross-sectional area, taken perpendicular to the longitudinal axis, which is smaller than the shaft cross-sectional area. The asymmetrically tapered portion includes a longitudinally aligned face extending substantially parallel to the longitudinal axis and an angled face extending at an acute angle to the longitudinal axis and oriented in lateral opposition to the longitudinally aligned face.

BRIEF DESCRIPTION OF THE DRAWINGS

For a better understanding, reference may be made to the accompanying drawings, in which.

DESCRIPTION OF ASPECTS OF THE DISCLOSURE

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 1:
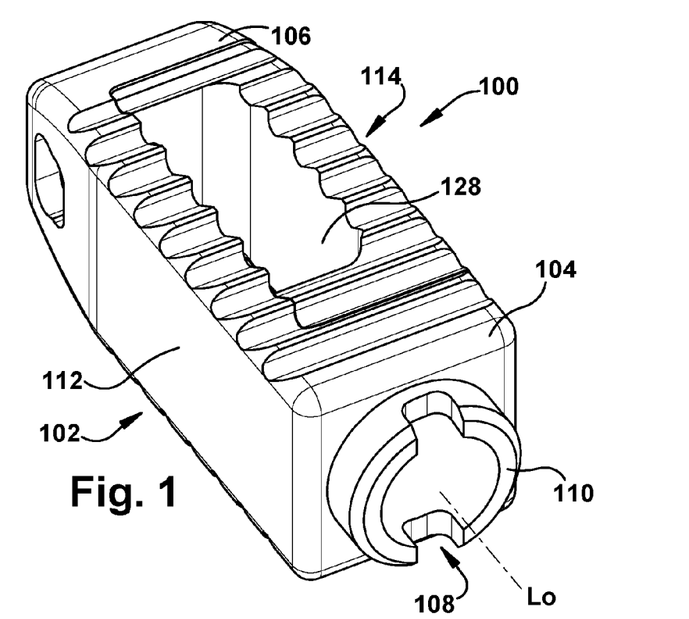
FIG. 1 is a perspective view of a spinal fusion cage in a first configuration.
Figure 2:
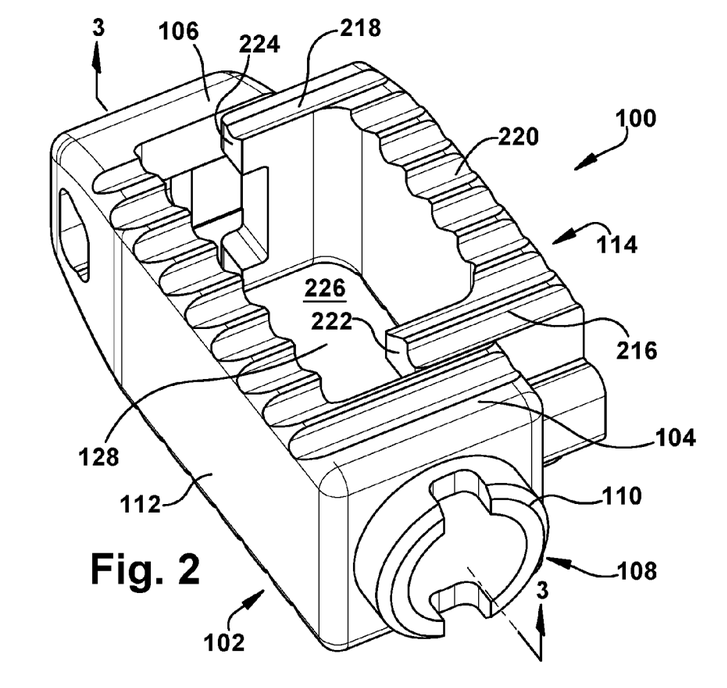
FIG. 2 is a perspective view of the spinal fusion cage of FIG. 1 in a second configuration.

FIGS. 1 and 2 depict a spinal fusion cage 100. The spinal fusion cage 100 includes an outer cage 102 having a proximal outer cage endwall 104 longitudinally spaced from a distal outer cage endwall 106. The longitudinal direction, for the sake of this description, is defined with respect to the spinal fusion cage 100 and is parallel to longitudinal axis Lo of FIG. 1. The proximal outer cage endwall 104 includes a tool aperture 108. The tool aperture 108 may include a collar 110, as shown, which could have a threaded outer or inner cylindrical surface to aid with engaging other tools/structures as will be discussed below. The outer cage 102 includes an outer cage sidewall 112 extending longitudinally between the proximal and distal outer cage endwalls 104 and 106.

The spinal fusion cage 100 also includes an inner cage 114 having a proximal inner cage endwall 216, shown in FIG. 2, longitudinally spaced from a distal inner cage endwall 218. The inner cage 114 includes an inner cage sidewall 220 extending longitudinally between the proximal and distal inner cage endwalls 216 and 218. The proximal and distal inner cage endwalls 216 and 218 are each in slidable contact with a corresponding one of the proximal and distal outer cage endwalls 104 and 106, such as via the tongue-and-groove connection shown in FIG. 2. The proximal and distal inner cage endwalls 216 and 218 each include an endwall contact surface (222 and 224, respectively) at a laterally opposite face of the proximal and distal inner cage endwalls 216 and 218 from the inner cage sidewall 220. The inner cage 114 selectively slides with respect to the outer cage 102 to transition the spinal fusion cage 100 between a retracted configuration, shown in FIG. 1, and an expanded configuration, shown in FIG. 2.

The inner and outer cage 102 and 114 collectively define a fusion cage cavity space 226. The fusion cage cavity space 226 has a volume which varies responsive to relative sliding of the inner cage 114 with respect to the outer cage 102.

The spinal fusion cage 100 may be made of any desired material(s) and have any suitable dimensions and/or physical features for a particular use environment. For example, portions of the outer and inner cages 102 and 114 may include serrations, as shown in the Figures, to resist pullout motion of the installed spinal cage. The distal outer cage endwall 106 can be slightly tapered or "bulleted", as shown, to aid insertion. The spinal fusion cage 100 may have a quadrilateral configuration, as shown in the Figures, and may be at least partially made of polyetheretherketone ("PEEK"). For example, the outer and inner cages 102 and 114 could each be at least partially made from PEEK. The spinal fusion cage 100 may have any desired dimensions, such as, but not limited to, about 9-11 mm retracted width, about 12.5-14.5 mm expanded width, about 23-32 mm length, about 8-16 mm height, and any combinations of these or other suitable dimensions. One or more radiopaque markers may be provided, to assist in fluoroscopic location and navigation during or after installation.

The spinal fusion cage 100 may include at least one opening 128, other than the tool aperture 108, in at least one of the inner cage 114 and the outer cage 102 (top and bottom openings 128 are shown being collectively formed by the inner and outer cages 114 and 102 in the Figures). The opening(s) 128, when present, permit direct fluid communication between the fusion cage cavity space 226 and a surrounding ambient (e.g., intervertebral) space. The opening(s) 128 may permit travel of graft material therethrough and/or may encourage bony ingrowth during the fusion process.

Figure 3:
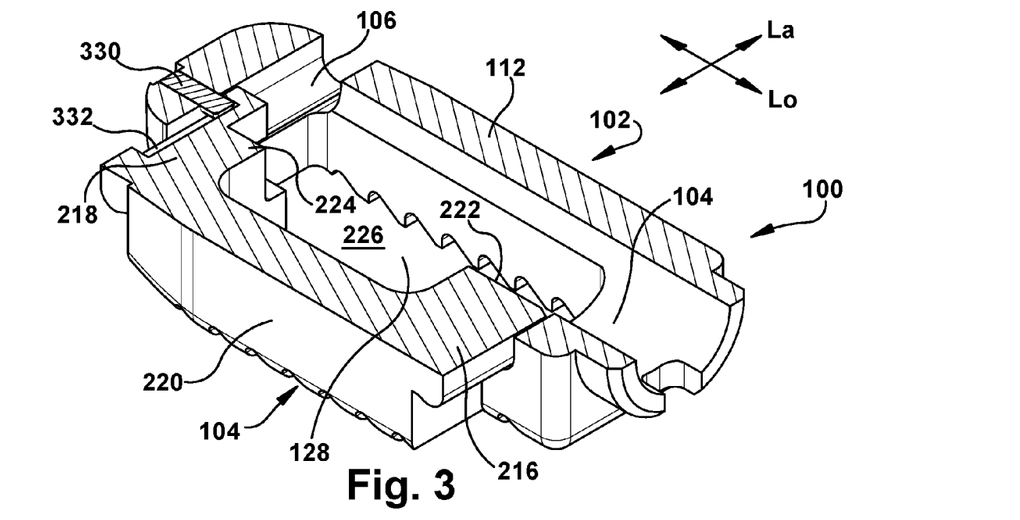
FIG. 3 is a cross-sectional view taken along line 3-3 of FIG. 2.

As shown in FIG. 3, a chosen one of the inner cage 114 and the outer cage 102 may include a pin 330 (e.g., a titanium pin) and the other one of the inner cage 114 and the outer cage 102 may include a groove 332 into which the pin 330 at least partially longitudinally protrudes. When present, the pin 330 and groove 332 may cooperatively block lateral travel of the inner cage 114 away from the outer cage 102 beyond a predetermined maximum travel distance, at which the spinal fusion cage 100 is in a fully expanded configuration. The "lateral" direction, for the purposes of this description, is substantially perpendicular to the longitudinal direction, as in the example lateral arrow La of FIG. 3.

Figure 4:
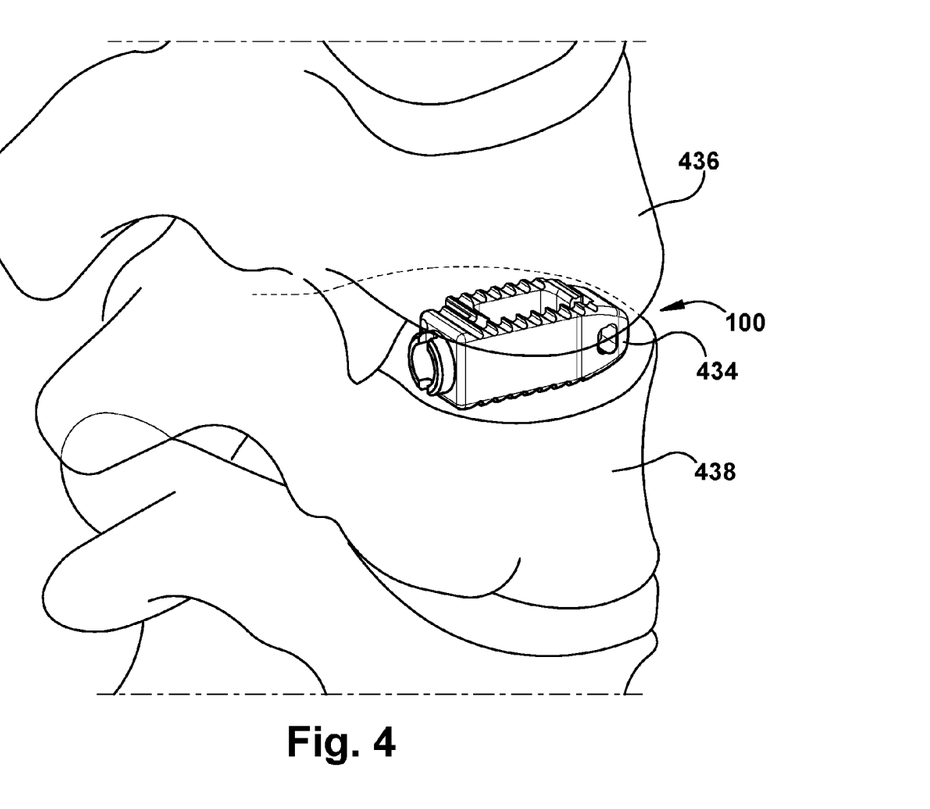
FIG. 4 is a schematic side view of the spinal fusion cage of FIG. 2 in an example use environment.

FIG. 4 depicts the spinal fusion cage 100 in an installed and fully expanded condition, located in the intervertebral disc 434 between upper and lower vertebrae 436 and 438, respectively. In inserting the spinal fusion cage 100, the intervertebral disc 434 is first exposed at surgery. The outer annular fibers are incised with a scalpel to create a window in the interior of the disc 434. The nucleus pulposus is evacuated via standard surgical technique, with care to remove the disc material toward the midline as well as laterally. If the procedure is being performed by a posterior route, annular windows should be constructed bilaterally. After the nucleus pulposus has been removed sufficiently and the endplates prepared suitably, the spinal fusion cage 100 can be inserted.

FIGS. 5-9 collectively depict an assortment of surgical tools and installation aids that may be used, singly or in combination, in the system for installing the spinal fusion cage 100.

Figures 5, 6, 7A, 7B, 8:
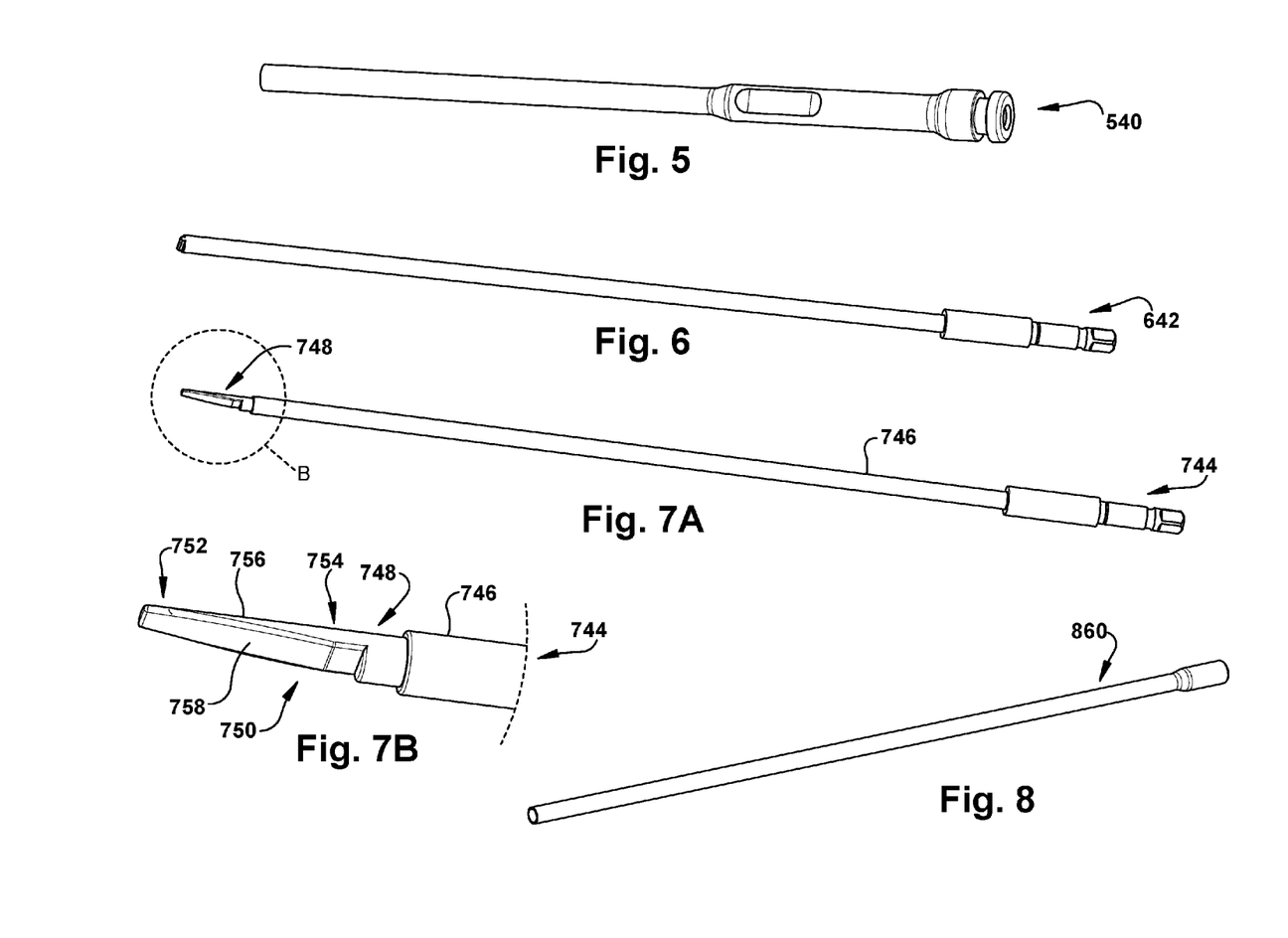
FIG. 5 is a side view of a tool for use during the installation of the spinal fusion cage of FIG. 1.
FIG. 6 is a side view of a tool for use during the installation of the spinal fusion cage of FIG. 1.
FIG. 7A is a side view of a tool for use during the installation of the spinal fusion cage of FIG. 1.
FIG. 7B is a detail view of area "B" of FIG. 7A.
FIG. 8 is a side view of a tool for use during the installation of the spinal fusion cage of FIG. 1.

FIG. 5 depicts an insertion tool 540 for selective rigid attachment to the tool aperture 108, such as by threadable attachment to the collar 110 of the tool aperture 108. The insertion tool 540 includes a longitudinally extending insertion lumen in fluid communication with the fusion cage cavity space 226. The insertion lumen selectively accepts at least a portion of another tool and/or a graft material therethrough during the installation process, in order to facilitate access to the fusion cage cavity space 226 from outside the patient's surgical wound. The insertion tool 540 can also be used to transmit manipulative force between a user and the spinal fusion cage 100, such as in maneuvering the spinal fusion cage 100 into a desired position in the intervertebral disc 434 and/or holding the spinal fusion cage 100 steady during the installation process.

FIG. 6 shows a counter torque tool 642 which can be selectively inserted through the insertion lumen of the insertion tool 540. The counter torque tool 642 can be used to selectively exert a rotational force upon the spinal fusion cage 100 as desired. For example, the counter torque tool 642 could engage a structure of the spinal fusion cage 100 (e.g., the slot of the collar 110) and then be rotated by a user to transfer a desired torque force, around the longitudinal axis Lo, to the spinal fusion cage 100. As another example, the counter torque tool 642 could be used to hold the spinal fusion cage 100 "steady" and counteract the force of the insertion tool 540 being screwed on to or off from the tool aperture 108, such as a threaded collar 110 of the tool aperture.

In FIGS. 7A-7B, an actuation tool 744 is depicted in detail. The actuation tool 744 includes an elongate shaft 746. The shaft has a shaft cross-sectional area, taken perpendicular to the longitudinal axis Lo. An operative portion 748 of the actuation tool 744 is shown in the detail view "B" of FIG. 7B. The operative portion 748, located longitudinally distal to the shaft 746, is configured for at least partial insertion in a distal direction through the tool aperture 108 into the fusion cage cavity space 226. The operative portion 748 of the actuation tool 744 has an asymmetrically tapered portion 750. The phrase "asymmetrically tapered" is used herein to indicate that the majority of the volume of this portion is arranged toward one lateral side of the longitudinal axis Lo. It is understood that there may be certain orientations or cut planes across which the asymmetrically tapered portion 750 might appear to be symmetrical, in a particular frame of reference, but any such carefully defined "local symmetry" will not destroy the general asymmetrical nature of the taper, as shown and discussed herein.

A distal end 752 of the asymmetrically tapered portion 750 of the operative portion 748 has a first cross-sectional area, taken perpendicular to the longitudinal axis Lo, which is smaller than the shaft 746 cross-sectional area. Optionally, a proximal portion 754 of the operative portion 748 which is located longitudinally between the distal end 752 and the shaft 746 may have a second cross-sectional area, taken perpendicular to the longitudinal axis Lo, which is larger than the first cross-sectional area (of the distal end 752) and is smaller than the shaft 746 cross-sectional area. The asymmetrically tapered portion 750 including a longitudinally aligned face 756 extending substantially parallel to the longitudinal axis Lo and an angled face 758 extending at an acute angle (as shown in the Figures) to the longitudinal axis Lo. The angled face 758 is substantially oriented in lateral opposition to the longitudinally aligned face 756, as shown.

Optionally, and also as shown in the Figures, the longitudinally aligned face 756 of the operative portion 748 of the actuation tool 744 may extend substantially parallel to (in the longitudinal direction), and concentric with (in the lateral direction), the longitudinal axis Lo—that is, may be "barrel-shaped" or rounded. Alternatively, though not shown, the longitudinally aligned face 756 may be substantially straight and tangent to the longitudinal direction and/or may have a curve which is not substantially concentric with the longitudinal axis Lo, though one of ordinary skill in the art will be able to readily provide a suitable actuation tool 744 for a particular use environment. The actuation tool 744 and its relation to the spinal fusion cage 100 will be discussed in detail with reference to FIGS. 11A-12C.

Turning to FIG. 8, a graft insertion tool 860 is shown. A distal end of the graft insertion tool 860 accepts and holds graft material. The graft insertion tool 860 is then selectively inserted through the insertion lumen of the insertion tool 540 to deliver the graft into the fusion cage cavity space 226. Thus, the graft insertion tool 860 is configured to selectively supply graft material to the fusion cage cavity space 226 when the actuation tool 744 is absent therefrom.

Figure 9:
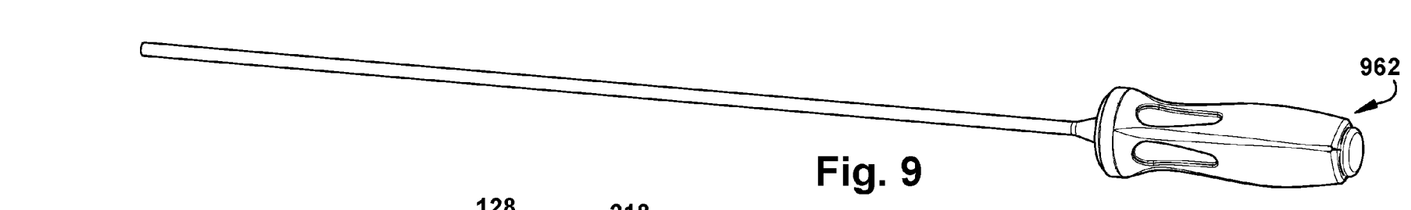
FIG. 9 is a side view of a tool for use during the installation of the spinal fusion cage of FIG. 1.

FIG. 9 depicts a graft pusher 962. The graft pusher 962 is selectively inserted through the insertion lumen of the insertion tool 540 to force graft into the fusion cage cavity space 226 and/or to provide an indication of the amount of graft material present within the fusion cage cavity space 226, such as with a graduated scale on the shaft of the graft loader 962.

Figure 10:
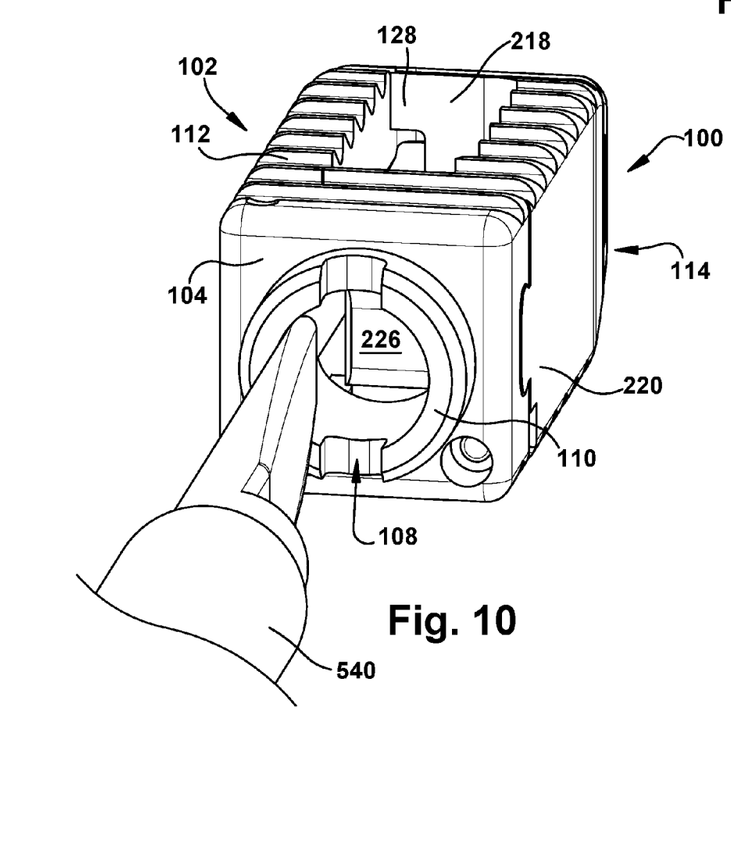
FIG. 10 is a front perspective view of the spinal fusion cage of FIG. 1 and the tool of FIGS. 7A-7B.

As shown in the front perspective view of FIG. 10, the actuation tool 744 may be configured for selective slidable insertion into the fusion cage cavity space 226, such as via the tool aperture 108. FIGS. 11A-12C will be referenced below to teach how, in effect, contact between (1) an inner face of the outer cage sidewall 220 and (2) the endwall contact surface 222 of the proximal inner cage endwall 216 with (3) the angled face 758 of the actuation tool 744 can urge the endwall contact surface 222 of the proximal inner cage endwall 216 laterally apart from the outer cage sidewall 220. Thus, the spinal fusion cage 100 can be brought into an at least partially expanded configuration via wedging action of the actuation tool 744 sliding longitudinally into and through the fusion cage cavity space 226, as will now be shown and described.

In a method of installing a spinal fusion cage 100 according to an aspect of this disclosure, the adjacent (upper and lower) vertebrae 436 and 438 and the intervertebral disc 434, along with any other structures of the intervertebral space, are prepared as desired to allow for placement of the spinal fusion cage 100, in a retracted configuration, between two adjacent vertebrae of a patient 436 and 438. For example, the user may expose an intervertebral disc 434 of the patient between the two adjacent vertebrae 436 and 438 and may then create a window in an interior of the disc 434. The user may remove nucleus pulposus from the intervertebral disc to create a disc cavity. The spinal fusion cage 100, in the retracted configuration (fully retracted, for most use environments), can then be placed at least partially within the disc cavity. This preparation results in a situation much like that shown in FIG. 4, although the initial insertion of the spinal fusion cage 100 is in a retracted configuration, not the expanded configuration shown in FIG. 4.

Once the retracted-configuration spinal fusion cage 100 is in place within the disc cavity, the process of laterally expanding the spinal fusion cage 100 can occur, as shown in detail in the partial views of FIGS. 11A-12C. It should be noted that, for most use environments, the depicted sequence of expansion will be done within the intervertebral space, but the patient spinal components are omitted from these Figures for clarity of depiction. Likewise, FIGS. 11A-12C are cutaway or cross-sectional views, to facilitate understanding of the inner structures and motions of the spinal fusion cage 100.

Figure 11A:
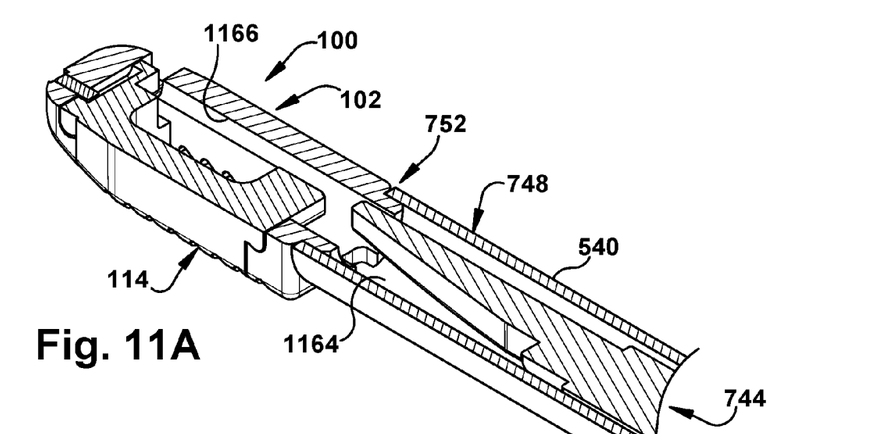
FIGS. 11A-11H are partial cross-sectional top views of the spinal fusion cage of FIG. 1 during an sequence of installation.
Figure 11B:
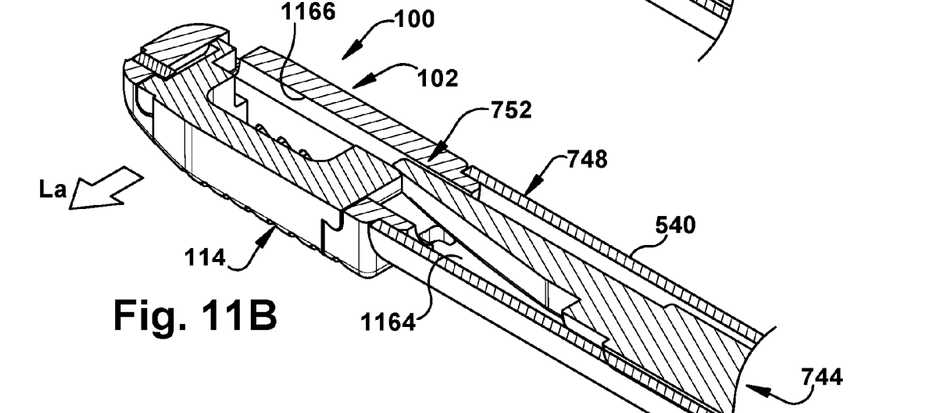
Figure 11C:
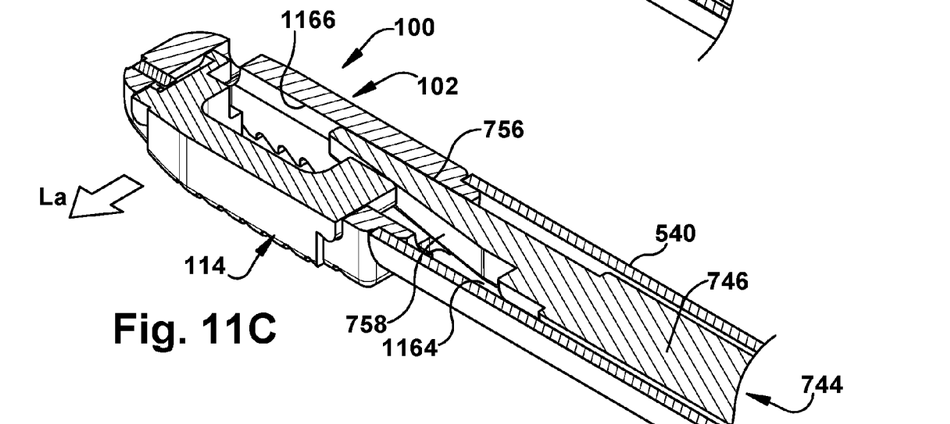

As shown in FIGS. 11A-12C, the insertion tool 540 is shown as being rigidly attached to the spinal fusion cage 100 throughout the depicted and described expansion process, but one of ordinary skill in the art could readily provide an alternate arrangement with no insertion tool 540. With reference to FIG. 11A, though, the actuation tool 744 is in the process of being inserted longitudinally into the insertion lumen 1164. That is, the actuation tool 744 is longitudinally aligned with the tool aperture 108, with the longitudinally aligned face 756 of the actuation tool 744 being directly adjacent an inner face 1166 of the outer cage sidewall 112. As shown in FIG. 11A, the operative portion 748 of the actuation tool 744 is longitudinally interposed between the shaft 746 of the actuation tool 744 and the spinal fusion cage 100 during the preparation step shown in FIG. 11A. Also as shown in FIG. 11A and moving through the subsequent views up until at least FIG. 11E, the distal end 752 of the operative portion 748 of the actuation tool 744 is moved into the fusion cage cavity space 226 via the tool aperture 108.

At least FIGS. 11B-11E illustrate the way in which continued, deeper penetration of the actuation tool 744 into the fusion cage cavity space 226 causes contact of the inner face 1166 of the outer cage sidewall 112 with the longitudinally aligned face 756 of the actuation tool 744 in a sliding manner. This contact between the longitudinally aligned face 756 and the inner face 1166 may occur concurrently with contact of the endwall contact surface 222 of the proximal inner cage endwall 216 with the angled face 758 of the actuation tool 744 in a sliding manner. Due to those sliding contacts, the endwall contact surface 222 of the proximal inner cage endwall 216 is urged laterally apart from the outer cage sidewall 112 into an at least partially expanded configuration via wedging action of the actuation tool 744 sliding longitudinally into and through the fusion cage cavity space 226, as shown in at least FIGS. 11B-11E. During this process, the actuation tool 744 is imposed laterally between the proximal inner cage endwall 216 and the outer cage sidewall 112. The actuation tool 744 optionally "braces" against the outer cage sidewall 112 to push the inner cage 114 laterally outward (i.e., in the direction of lateral arrow "Lo") via contact with the proximal inner cage endwall 216.

Figures 11D, 11E, 11F:
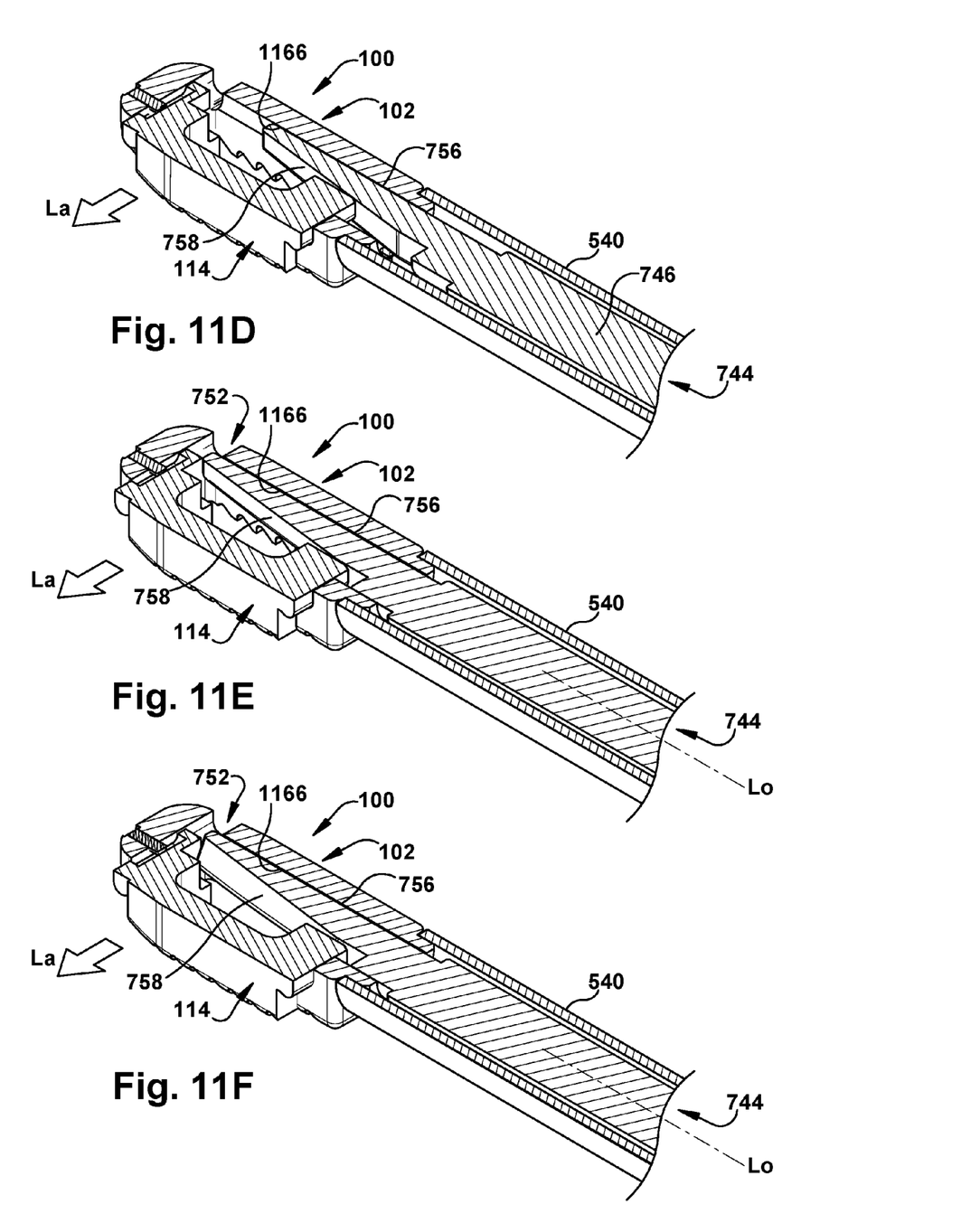
Figure 11G:
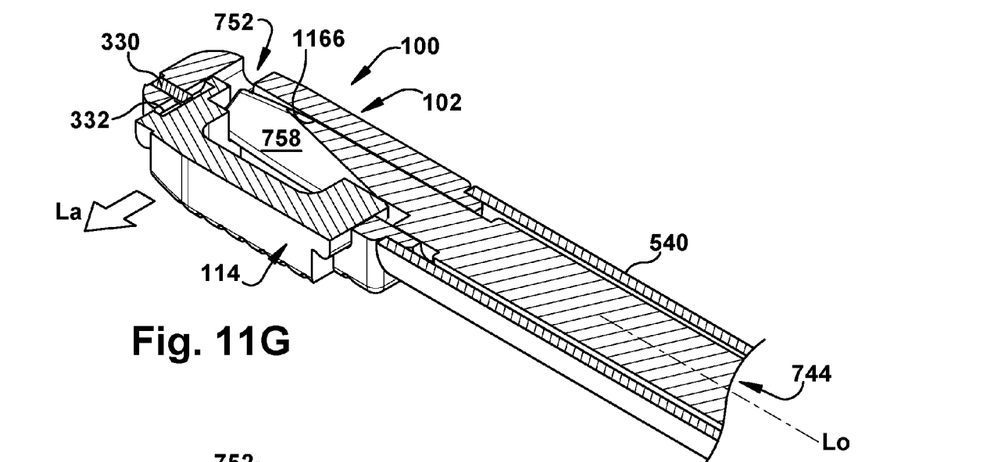
Figure 11H:
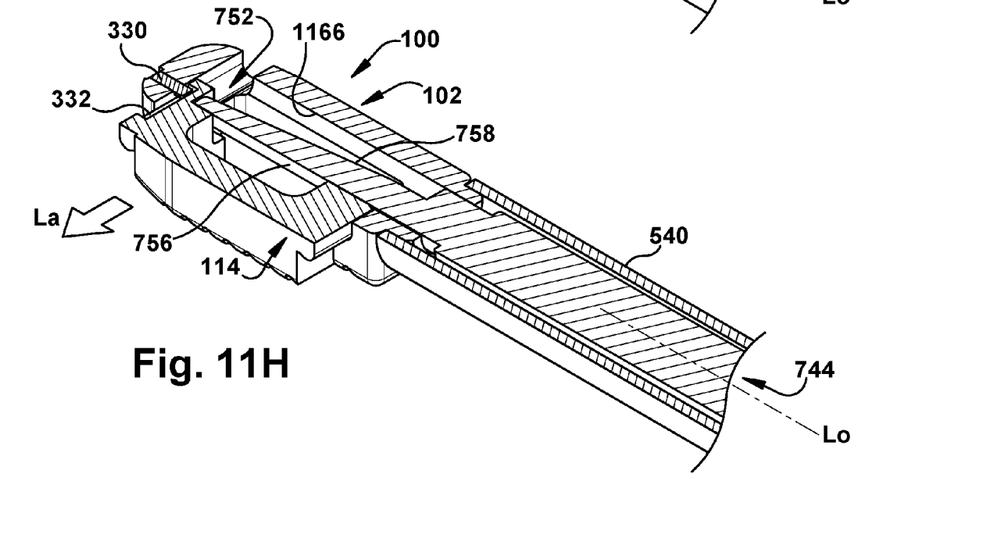
Figure 12A:
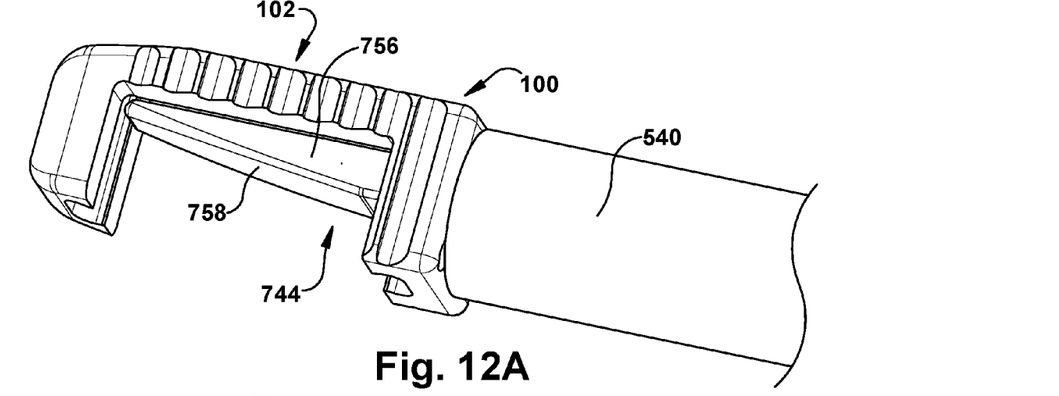
FIGS. 12A-12C are partial closed top views corresponding to the cross-sectional top views of FIGS. 11F-11H, respectively.
Figure 12B:
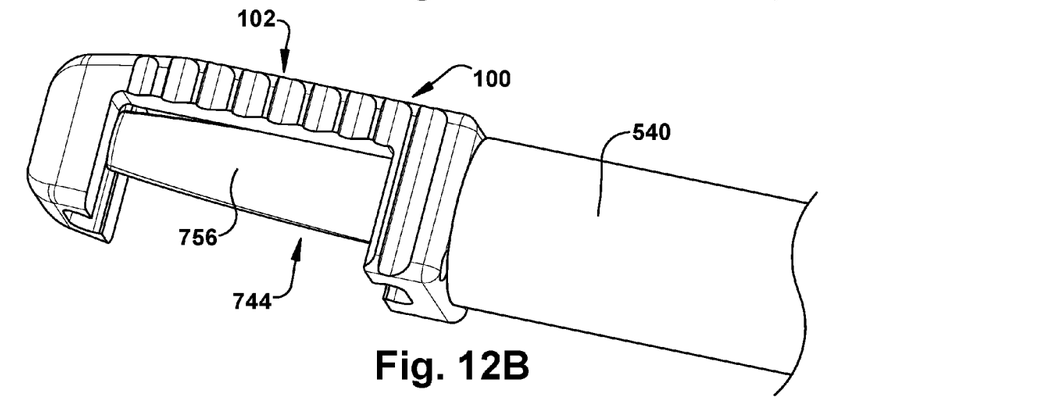
Figure 12C:
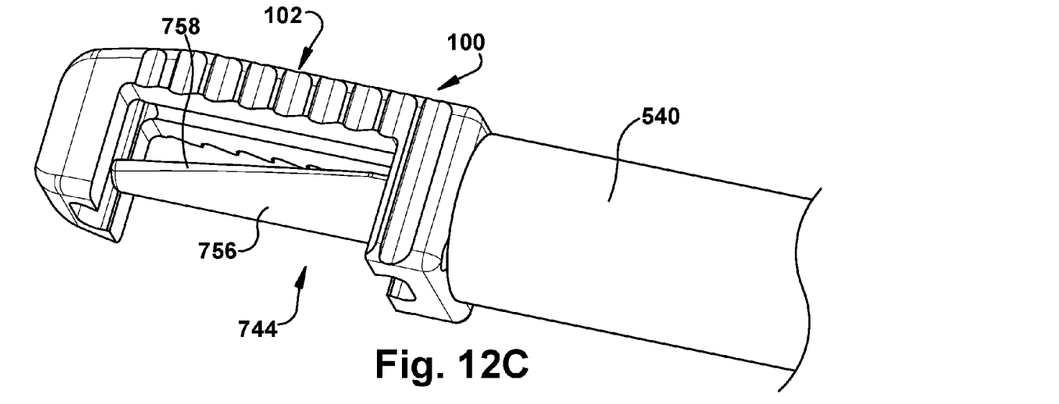

As shown in the sequence of at least FIGS. 11B-11E, with the actuation tool 744 being imposed laterally between the proximal inner cage endwall 216 and the outer cage sidewall 112, the actuation tool 744 is gradually inserted more deeply into the tool aperture 108. As a result, the operative portion 748 of the actuation tool 744 is further inserted into the fusion cage cavity space 226 via the tool aperture 108 to achieve a predetermined depth of insertion, shown in FIG. 11E of the actuation tool 744 into the spinal fusion cage 100. Once the actuation tool 744 is at the predetermined depth of insertion, the actuation tool 744 may be rotated, at that predetermined depth of insertion, a predetermined amount clockwise and/or, sequentially, counterclockwise about the longitudinal axis. This rotation of the actuation tool 744 (while held at the predetermined depth of insertion) by the predetermined amount acts to bring the distal end 752 of the operative portion 748 of the actuation tool 744 into contact with the distal inner cage endwall 218, as shown in the sequence of FIGS. 11F-11H (a different perspective of which is shown in FIGS. 12A-12C, respectively). As shown in the sequence of FIGS. 11F-11H, the endwall contact surface 224 of the distal inner cage endwall 218 may be urged laterally apart from the outer cage sidewall 112 to bring the inner cage 114 into an at least partially expanded configuration via contact with the operative portion 748 of the actuation tool 744 during rotation of the actuation tool 744.

More specifically, the actuation tool 744 is placed at the predetermined depth of insertion, which is often a depth at which the distal end 752 is laterally adjacent, though not necessarily touching, the endwall contact surface 224 of the distal inner cage endwall 218. Indication of this achievement of the predetermined depth of insertion may be provided to the user via physical feedback, such as "bottoming out" of the actuation tool 744 against the distal inner and/or outer cage endwall 218 or 106, and/or through visual and/or physical interaction of the shaft 746 of the actuation tool 744 with a proximal-most portion (not shown) of the insertion tool 540. The actuation tool 744 is then rotated, at the predetermined depth of insertion, a predetermined amount. This predetermined amount of rotation could be in the range of about 20-150°, and, more specifically, about 45-90°. Though this rotation will usually be centered on (e.g., concentric to) the longitudinal axis Lo, a different center of rotation could be chosen for a particular use environment. During this rotation of the actuation tool 744, the longitudinally aligned face 756 of the operative portion 748 of the actuation tool 744 slides against at least one of the endwall contact surfaces 222, 224 of the proximal and distal inner cage endwalls 216, 218.

This sliding motion will occur along a direction substantially perpendicular to the longitudinal axis Lo, such as, but not limited to, within a lateral plane. Accordingly, the distal end 752 of the operative portion 748 of the actuation tool 744 is, as previously mentioned, brought into contact with the distal inner cage endwall 218 to push or urge the endwall contact surface 224 of the distal inner cage endwall 218 away from the outer cage sidewall 112, as particularly shown in FIGS. 11G-11H. Thus, the spinal fusion cage 100 is brought into an at least partially expanded configuration via contact between some structure(s) of the inner cage 114 and the operative portion 748 of the actuation tool 744 during rotation of the actuation tool 744.

Depending upon the relative designs and rigidities of the structures involved, the urging or pushing of the endwall contact surface 222 of the proximal inner cage endwall 216 laterally apart from the outer cage sidewall 112 may occur at a different, often earlier, time from the urging or pushing of the endwall contact surface 224 of the distal inner cage endwall 218 laterally apart from the outer cage sidewall 112. Accordingly, when the spinal fusion cage 100 is in a partially expanded configuration such as those configurations shown in at least FIGS. 11B-11G, the inner cage sidewall 220 may be angled relative to the longitudinal axis Lo with the proximal inner cage endwall 216 being located slightly laterally further from the outer cage sidewall 112 than is the distal inner cage endwall 218. As a result, the inner cage sidewall 220 may be tipped at an acute angle to the longitudinal axis Lo during at least a portion of the transition of the spinal fusion cage 100 between fully retracted and fully expanded conditions.

As shown particularly in FIGS. 11E-11H, a pin-in-groove mechanism is provided through cooperative structures on the inner cage 114 (groove 332) and the outer cage 102 (pin 330). When the spinal fusion cage 100 has achieved a fully expanded configuration at a maximum travel distance of the inner cage 114 with respect to the outer cage 102, the pin-in-groove mechanism at least partially blocks further lateral travel of the inner cage 114 away from the outer cage 102. This fully expanded configuration is shown in FIG. 11H.

As a general note, the spinal fusion cage 100 can be in a fully retracted position, shown in at least FIG. 11A, a fully expanded condition, shown in at least FIG. 11H, or any of a nearly infinite range of intermediate partially expanded conditions, shown in at least FIGS. 11C-11G. While many use environments of the spinal fusion cage 100 will include insertion into the intervertebral disc 434 in the fully retracted condition and then expansion into the fully expanded condition, and maintenance there, during/after the surgery, it is also contemplated that the spinal fusion cage 100 could be inserted into, and/or remain within, the intervertebral disc 434 in a partially expanded condition, if desired. However, it should be understood that, in the described sequence of FIGS. 11A-11H, the fully expanded configuration of the spinal fusion cage 100 is achieved at a maximum (e.g., a maximum allowable) travel distance of the inner cage 114 with respect to the outer cage 102. Placement of the inner cage 114 at the maximum travel distance with respect to the outer cage 102 is caused, in the aspect of FIGS. 11A-11H, by contact between each of the endwall contact surfaces 222, 224 of the proximal and distal inner cage endwalls 216, 218 and the operative portion 748 of the actuation tool 744.

Once the spinal fusion cage 100 is in place in the intervertebral space, the actuation tool 744 can be removed from the fusion cage cavity space 226 while the spinal fusion cage 100 is in an at least partially (up to fully) expanded configuration. Once the fusion cage cavity space 226 is vacated by the actuation tool 744, graft material can be placed within the fusion cage cavity space 226, such as through use of a graft insertion tool 860 and/or a graft pusher 962. Graft material can be added to the fusion cage cavity space 226 at any desired time before, during, and/or after installation of the spinal fusion cage 100, including while the spinal fusion cage 100 is in a fully retracted, partially expanded, and/or fully expanded condition. Optionally, the volume and/or insertion trajectory of the graft material into the fusion cage cavity space 226 may be selected to facilitate outflow of graft material from the fusion cage cavity space 226 through the opening(s) 128 and into the intervertebral space around the spinal fusion cage 100.

At any point before, during, and/or after expansion of the spinal fusion cage 100 and/or insertion of graft material into the fusion cage cavity space 226, the insertion tool 540 and/or a counter torque tool 642 could be used to reposition the spinal fusion cage 100 as desired. Once the spinal fusion cage 100 is in position and expanded as desired, and any desired graft material has been provided, the surgical tools (including the insertion tool 540) can be removed from the spinal fusion cage 100 and the surgical wound, and the surgical wound can be closed to conclude the surgery.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. For example, graft material could be placed within the fusion cage cavity space 226 before, during, and/or after lateral expansion of the spinal fusion cage 100. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate subcomponents, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. A method of installing a spinal fusion cage, the method comprising:
    providing a spinal fusion cage, including
        an outer cage having a proximal outer cage endwall longitudinally spaced from a distal outer cage endwall, the proximal outer cage endwall including a tool aperture, the outer cage including an outer cage sidewall extending longitudinally between the proximal and distal outer cage endwalls, and
        an inner cage having a proximal inner cage endwall longitudinally spaced from a distal inner cage endwall, the inner cage including an inner cage sidewall extending longitudinally between the proximal and distal inner cage endwalls, the proximal and distal inner cage endwalls each being in slidable contact with a corresponding one of the proximal and distal outer cage endwalls, and the proximal and distal inner cage endwalls each including an endwall contact surface at a laterally opposite face of the proximal and distal inner cage endwalls from the inner cage sidewall,
        the inner cage selectively sliding with respect to the outer cage to transition the spinal fusion cage between retracted and expanded configurations,
        the inner and outer cage collectively defining a fusion cage cavity space, the fusion cage cavity space having a volume which varies responsive to relative sliding of the inner cage with respect to the outer cage;
    providing an actuation tool including
        a shaft having a shaft cross-sectional area, taken perpendicular to a longitudinal axis,
        an operative portion, located longitudinally distal to the shaft, configured for at least partial insertion in a distal direction through the tool aperture into the fusion cage cavity space, the operative portion of the actuation tool having an asymmetrically tapered portion, a distal end of the asymmetrically tapered portion having a first cross-sectional area, taken perpendicular to the longitudinal axis, being smaller than the shaft cross-sectional area, the asymmetrically tapered portion including a longitudinally aligned face extending substantially parallel to the longitudinal axis and an angled face extending at an acute angle to the longitudinal axis and oriented in lateral opposition to the longitudinally aligned face;
    placing the spinal fusion cage, in the retracted configuration, between two adjacent vertebrae of a patient;
    longitudinally aligning the actuation tool with the tool aperture, with the longitudinally aligned face being directly adjacent an inner face of the outer cage sidewall, and the operative portion of the actuation tool being longitudinally interposed between the shaft of the tool and the spinal fusion cage;
    inserting the distal end of the operative portion of the actuation tool into the fusion cage cavity space via the tool aperture;
    contacting the inner face of the outer cage sidewall with the longitudinally aligned face of the actuation tool in a sliding manner;
    contacting the endwall contact surface of the proximal inner cage endwall with the angled face of the actuation tool in a sliding manner;
    urging the endwall contact surface of the proximal inner cage endwall laterally apart from the outer cage sidewall into an at least partially expanded configuration via wedging action of the actuation tool sliding longitudinally into and through the fusion cage cavity space, the actuation tool being imposed laterally between the proximal inner cage endwall and the outer cage sidewall;
    with the actuation tool being imposed laterally between the proximal inner cage endwall and the outer cage sidewall, further inserting the operative portion of the actuation tool into the fusion cage cavity space via the tool aperture to achieve a predetermined depth of insertion of the actuation tool into the spinal fusion cage;
    rotating the actuation tool, at the predetermined depth of insertion, a predetermined amount about the longitudinal axis to bring the distal end of the operative portion of the actuation tool into contact with the distal inner cage endwall; and
    urging the endwall contact surface of the distal inner cage endwall laterally apart from the outer cage sidewall into an at least partially expanded configuration via contact with the operative portion of the actuation tool during rotation of the actuation tool.

2. The method of claim 1, including achieving a fully expanded configuration of the spinal fusion cage at a maximum travel distance of the inner cage with respect to the outer cage, placement of the inner cage at the maximum travel distance with respect to the outer cage being caused by contact between the endwall contact surfaces of the proximal and distal inner cage endwalls and the operative portion of the actuation tool.

3. The method of claim 2, wherein providing a spinal fusion cage includes providing a pin-in-groove mechanism through cooperative structures on the inner cage and the outer cage, and wherein achieving a fully expanded configuration of the spinal fusion cage at a maximum travel distance of the inner cage with respect to the outer cage includes blocking, with the pin-in-groove mechanism, further lateral travel of the inner cage away from the outer cage.

4. The method of claim 1, including:
    removing the actuation tool from the fusion cage cavity space while the spinal fusion cage is in an at least partially expanded configuration; and
    placing graft material within the fusion cage cavity space, once vacated by the actuation tool.

5. The method of claim 2, including
    removing the actuation tool from the fusion cage cavity space while the spinal fusion cage is in an at least partially expanded configuration; and
    placing graft material within the fusion cage cavity space, once vacated by the actuation tool.

6. The method of claim 1, wherein providing a spinal fusion cage includes providing at least one opening, other than the tool aperture, to at least one of the inner cage and the outer cage, the opening permitting direct fluid communication between the fusion cage cavity space and a surrounding ambient space.

7. The method of claim 1, wherein providing a spinal fusion cage includes providing a spinal fusion cage having a quadrilateral configuration.

8. The method of claim 1, wherein placing the spinal fusion cage, in the retracted configuration, between two adjacent vertebrae of a patient includes:
    exposing an intervertebral disc between the two adjacent vertebrae and creating a window in an interior of the disc;
    removing nucleus pulposus from the disc to create a disc cavity; and
    placing the spinal fusion cage, in the retracted configuration, at least partially within the disc cavity.

9. The method of claim 1, wherein providing an actuation tool includes providing an operative portion having a longitudinally aligned face which extends substantially parallel to (in the longitudinal direction), and concentric with (in the lateral direction), the longitudinal axis.

10. The method of claim 1, wherein the urging of the endwall contact surface of the proximal inner cage endwall laterally apart from the outer cage sidewall occurs at a different time from the urging of the endwall contact surface of the distal inner cage endwall laterally apart from the outer cage sidewall, such that, when the spinal fusion cage is in the partially expanded configuration, the inner cage sidewall is angled relative to the longitudinal axis with the proximal inner cage endwall laterally further from the outer cage sidewall than is the distal inner cage endwall.

11. The method of claim 1, wherein rotating the actuation tool, at the predetermined depth of insertion, a predetermined amount includes sliding the longitudinally aligned face of the operative portion of the actuation tool against at least one of the endwall contact surfaces of the proximal and distal inner cage endwalls, the sliding occurring in a direction substantially perpendicular to the longitudinal axis.

12. A system for installing a spinal fusion cage, the system comprising:
    the spinal fusion cage, including
        an outer cage having a proximal outer cage endwall longitudinally spaced from a distal outer cage endwall, the proximal outer cage endwall including a tool aperture, the outer cage including an outer cage sidewall extending longitudinally between the proximal and distal outer cage endwalls, and
        an inner cage having a proximal inner cage endwall longitudinally spaced from a distal inner cage endwall, the inner cage including an inner cage sidewall extending longitudinally between the proximal and distal inner cage endwalls, the proximal and distal inner cage endwalls each being in slidable contact with a corresponding one of the proximal and distal outer cage endwalls, and the proximal and distal inner cage endwalls each including an endwall contact surface at a laterally opposite face of the proximal and distal inner cage endwalls from the inner cage sidewall,
        the inner cage selectively sliding with respect to the outer cage to transition the spinal fusion cage between retracted and expanded configurations,
        the inner and outer cages collectively defining a fusion cage cavity space, the fusion cage cavity space having a volume which varies responsive to relative sliding of the inner cage with respect to the outer cage; and
    an actuation tool including
        a shaft having a shaft cross-sectional area, taken perpendicular to a longitudinal axis,
        an operative portion, located longitudinally distal to the shaft, configured for at least partial insertion in a distal direction through the tool aperture into the fusion cage cavity space, the operative portion of the actuation tool having an asymmetrically tapered portion, a distal end of the operative portion having a first cross-sectional area, taken perpendicular to the longitudinal axis, being smaller than the shaft cross-sectional area, the asymmetrically tapered portion including a longitudinally aligned face extending substantially parallel to the longitudinal axis and an angled face extending at an acute angle to the longitudinal axis and oriented in lateral opposition to the longitudinally aligned face.

13. The system of claim 12, wherein the actuation tool is configured for selective slidable insertion into the fusion cage cavity space, contact between an inner face of the outer cage sidewall and the endwall contact surface of the proximal inner cage endwall with the angled face of the actuation tool urging the endwall contact surface of the proximal inner cage endwall laterally apart from the outer cage sidewall into an at least partially expanded configuration via wedging action of the actuation tool sliding longitudinally into and through the fusion cage cavity space.

14. The system of claim 13, wherein the actuation tool is configured to be rotated, at a predetermined depth of insertion into the fusion cage cavity space, a predetermined amount to bring the distal end of the operative portion of the actuation tool into contact with the distal inner cage endwall and thereby urge the endwall contact surface of the distal inner cage endwall laterally apart from the outer cage sidewall into an at least partially expanded configuration via contact with the operative portion of the actuation tool during rotation of the actuation tool.

15. The system of claim 12, wherein a chosen one of the inner cage and the outer cage includes a pin and an other one of the inner cage and the outer cage includes a groove into which the pin at least partially longitudinally protrudes, and wherein the pin and groove cooperatively block lateral travel of the inner cage away from the outer cage beyond a predetermined maximum travel distance, at which the spinal fusion cage is in a fully expanded configuration.

16. The system of claim 12, including a graft insertion tool configured to selectively supply graft material to the fusion cage cavity space when the actuation tool is absent therefrom.

17. The system of claim 12, wherein the spinal fusion cage includes at least one opening, other than the tool aperture, in at least one of the inner cage and the outer cage, the opening permitting direct fluid communication between the fusion cage cavity space and a surrounding ambient space.

18. The system of claim 12, wherein the spinal fusion cage has a quadrilateral configuration.

19. The system of claim 12, wherein the longitudinally aligned face of the operative portion of the actuation tool extends substantially parallel to (in the longitudinal direction), and concentric with (in the lateral direction), the longitudinal axis.

20. The system of claim 12, wherein a proximal portion of the operative portion of the actuation tool which is located longitudinally between the distal end and the shaft has a second cross-sectional area, taken perpendicular to the longitudinal axis, which is larger than the first cross-sectional area and smaller than the shaft cross-sectional area.

21. The system of claim 12, including
an insertion tool for selective rigid attachment to the tool aperture, the insertion tool including a longitudinally extending insertion lumen in fluid communication with the fusion cage cavity space, the insertion lumen selectively accepting at least a portion of the actuation tool therethrough, and the insertion tool transmitting manipulative force between a user and the spinal fusion cage.

* * * * *